(12) United States Patent
Tiemessen

(10) Patent No.: US 6,239,102 B1
(45) Date of Patent: May 29, 2001

(54) PHARMACEUTICAL COMPOSITIONS

(75) Inventor: Harry Tiemessen, Weil-Haltingen (DE)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/091,072

(22) PCT Filed: Jan. 20, 1997

(86) PCT No.: PCT/EP97/00252

§ 371 Date: Jun. 9, 1998

§ 102(e) Date: Jun. 9, 1998

(87) PCT Pub. No.: WO97/25977

PCT Pub. Date: Jul. 24, 1997

(30) Foreign Application Priority Data

Jan. 19, 1996 (GB) .................................................. 9601120

(51) Int. Cl.⁷ .................................................. A61K 38/00
(52) U.S. Cl. .................................................. 514/9; 514/11
(58) Field of Search .................................................. 514/9, 11

(56) References Cited

FOREIGN PATENT DOCUMENTS

| 296122 A2 | * 12/1988 | (DE) . |
| 296122 | 12/1988 | (EP) . |
| 0315079 | 5/1989 | (EP) . |
| 0317120 | 5/1989 | (EP) . |
| 0331755 | 9/1989 | (EP) . |
| 0570829 | 11/1993 | (EP) . |
| 589843 | 3/1994 | (EP) . |
| WO 95/31969 | * 11/1995 | (FI) . |
| 2222770 | 3/1990 | (GB) . |
| 2269536 | 2/1994 | (GB) . |
| 147892 | 5/1991 | (JP) . |
| 8806438 | 9/1988 | (WO) . |
| 93/20833 | 10/1993 | (WO) . |

OTHER PUBLICATIONS

Osol, Editor of Remington's Pharmaceutical Sciences, 15th Edition, pp. 1252 and 1253, Jun. 11, 1976.*
Windholz, Editor of The Merck Index, 10th Edition, pp. 6706–6707, Jul. 21, 1986.*
Derwent Abstract of JP 04253907, (Green Cross Corp.) (1992).
Derwent Abstract of DD 295766 (Arzneimittelwerk Dresda) (1991).

* cited by examiner

Primary Examiner—Dwayne C. Jones
(74) Attorney, Agent, or Firm—John D. Thallemer

(57) ABSTRACT

A process for preparing an emulsion composition comprising a cyclosporin, a rapamycin or an ascomycin or a derivative thereof as active agent, which process comprises the step of admixing to a placebo fat emulsion a concentrate comprising
a) the active agent,
b) a stabiliser selected from a phospholipid, a glycolipid, a sphingolipid, a diacylphosphatidyl glycerol, an egg-phosphatidylglycerol, a soy-phosphatidylglycerol, a diacylphosphatidylglycerol, or a salt thereof; or a saturated, mono- or di-unsaturated ($C_{12-24}$) fatty acid, or a salt thereof, and
c) an organic solvent,
wherein the weight ratio of active agent to stabiliser is between 400:1 and 0.5:1.

The invention also provides ready-to-use emulsions, e.g. for intravenous administration, prepared using the above process.

7 Claims, 1 Drawing Sheet

PHARMACEUTICAL COMPOSITIONS

This application is a 371 of PCT/EP97/00252 with a filing date of Jan. 20, 1997.

FIELD OF THE INVENTION

This invention relates to a pharmaceutical composition having as active ingredient a cyclosporin, a cyclosporin derivative that is useful in the treatment of multi-drug resistance syndrome, or a macrolide e.g. a rapamycin or an ascomycin. In particular this invention relates to a pharmaceutical composition containing [3'-desoxy-3'-oxo-MeBmt]$^1$-[Val]$^2$-Ciclosporin (PSC 833) as active ingredient.

BACKGROUND OF THE INVENTION

The resistance of tumour cells to chemotherapeutics is a major factor in the failure of chemotherapy. One form of resistance to chemotherapeutics is "multi-drug resistance" where the tumour cells become cross-resistant to a variety of chemotherapeutics; for example alkaloids, anthracyclines, actinomycin D, adriamycin and colchicine. Multi-drug resistance syndrome has been correlated in many reports with the overexpression of transmembrane glycoproteins called P-glycoproteins (Pgp). Cyclosporins have been found to reverse multi-drug resistance syndrome and [3'-desoxy-3'-oxo-MeBmt]$^1$-[Val]$^2$-Ciclosporin in particular has been found to be effective. [3'-desoxy-3'-oxo-MeBmt]$^1$-[Val]$^2$-Ciclosporin and its utility is described in European patent publication No. 296 122.

The cyclosporins comprise a class of structurally distinctive, cyclic, poly-N-methylated undecapeptides, generally possessing pharmacological, in particular immunosuppressive, anti-inflammatory and/or anti-parasitic activity, each to a greater or lesser degree. Cyclosporins are generally not readily soluble in aqueous media. Consequently, it is difficult to develop pharmaceutically acceptable carriers which allow delivery of the drug in sufficiently high concentrations to permit convenient use and which allow efficient and consistent absorption of the drug by the body. Often individual cyclosporins present very specific problems in relation to their administration and, in particular, in providing galenic formulations. Species specific problems also arise with regard to drug bioavailability. This is particularly the case with the compound [3'-desoxy-3'-oxo-MeBmt]$^1$-[Val]$^2$-Ciclosporin which presents very special problems in relation to its incorporation in galenic formulations.

To deal with the general problems of formulating cyclosporins, British patent application 2222770 A discloses galenic formulations, containing cyclosporins, that are in the form of microemulsions or microemulsion preconcentrates. These formulations comprise a hydrophilic phase, a lipophilic phase and a surfactant. The following components are described as suitable for the hydrophilic phase: Transcutol, Glycofurol and 1,2-propylene glycol. Medium chain fatty acid triglycerides are disclosed as being suitable for the lipophilic phase. Reaction products of natural or hydrogenated vegetable oils and ethylene glycol are given as surfactants. However this British patent application does not deal with the problems of formulating [3'-desoxy-3'-oxo-MeBmt]$^1$-[Val]$^2$-Ciclosporin which is much more lipophilic than most other cyclosporins. PCT appliction publication no. WO 93/20833 discloses surfactant-containing compositions of [3'-desoxy-3'-oxo-MeBmt]$^1$-[Val]$^2$-Ciclosporin in which Cremophor is a preferred surfactant.

Rapamycin is an immunosuppressive lactam macrolide produceable, for example by *Streptomyces hygroscopicus*. The structure of rapamycin is given in Kesseler, H., et al.; 1993; *Helv. Chim. Acta;* 76: 117. Rapamycin is an extremely potent immunosuppressant and has also been shown to have antitumor and antifungal activity. Its utility as a pharmaceutical, however, is restricted by its very low and variable bioavailability. Moreover, rapamycin is highly insoluble in aqueous media, e.g. water, making it difficult to formulate stable galenic compositions. Numerous derivatives of rapamycin are known. Certain 16-O-substituted rapamycins are disclosed in WO 94/02136, the contents of which are incorporated herein by reference. 40-O-substituted rapamycins are described in, e.g., in U.S. Pat. No. 5,258,389 and WO 94/09010 (O-aryl and O-alkyl rapamycins); WO 92/05179 (carboxylic acid esters), U.S. Pat. No. 5,118,677 (amide esters), U.S. Pat. No. 5,118,678 (carbamates), U.S. Pat. No. 5,100,883 (fluorinated esters), U.S. Pat. No. 5,151,413 (acetals), U.S. Pat. No. 5,120,842 (silyl ethers), WO 93/11130 (methylene rapamycin and derivatives), WO 94/02136 (methoxy derivatives), WO 94/02385 and WO 95/14023 (alkenyl derivatives) all of which are incorporated herein by reference. 32-O-dihydro or substituted rapamycin are described, e.g., in U.S. Pat. No. 5,256,790, incorporated herein by reference.

Further rapamycin derivatives are described in PCT application number EP96/02441, for example 32-deoxorapamycin as described in Example 1, and 16-pent-2-ynyloxy-32(S)-dihydrorapamycin as described in Examples 2 and 3. The contents of PCT application number EP96/02441 are incorporated herein by reference.

The rapamycin used in the compositions of this invention may be any rapamycin or derivative thereof, for example as disclosed above or in the above-mentioned patent applications.

Thus the rapamycin used in the compositions of this invention may be rapamycin or an O-substituted derivative in which the hydroxyl group on the cyclohexyl ring of rapamycin is replaced by $—OR_1$ in which $R_1$ is hydroxyalkyl, hydroxyalkoxyalkyl, acylaminoalkyl and aminoalkyl; e.g. as described in WO94/09010, for example 40-O-(2-hydroxy)ethyl-rapamycin, 40-O-(3-hydroxy)propyl-rapamycin, 40-O-[2-(2-hydroxy)ethoxy]ethyl-rapamycin and 40-O-(2-acetaminoethyl)-rapamycin. The rapamycin derivative may be a 26- or 28-substituted derivative.

Preferred rapamycins for use in the compositions of this invention include rapamycin, 40-O-(2-hydroxy)ethyl rapamycin, 32-deoxorapamycin and 16-pent-2-ynyloxy-32(S)-dihydrorapamycin. A more preferred rapamycin is 40-O-(2-hydroxy)ethyl rapamycin. Numbering of rapamycin derivatives as used herein refers to the structure disclosed as Formula A at page 4 of published PCT application WO 96/13273, the contents of which are incorporated herein by reference.

Ascomycins, of which FK-506 and ascomycin are the best known, comprise another class of lactam macrolides, many of which have potent immunosuppressive and anti-inflammatory activity. FK506 is a lactam macrolide immunosuppressant that is produced by *Streptomyces tsukubaensis* No 9993. The structure of FK506 is given in the appendix to the Merck Index, 11th ed. (1989) as item A5. Ascomycin is described, e.g., in U.S. Pat. No. 3,244,592. Many derivatives of ascomycin and FK-506 have been synthesized, including halogenated derivatives such as 33-epi-chloro-33-desoxy-ascomycin described in EP 427 680. Ascomycin, FK-506 and their structurally similar analogues and derivatives are termed collectively "ascomycins".

Examples of compounds of the ascomycin or FK 506 class are those mentioned above. They include for example FK 506, ascomycin and other naturally occurring compounds. They include also synthetic analogues.

A preferred compound of the FK 506 class for use as active ingredient in the present invention is disclosed in EP 427 680, e.g. Example 66a also known as 33-epi-chloro-33-desoxy-ascomycin. Other preferred compounds are disclosed in EP 465 426, and in EP 569 337, e.g. the compound disclosed under Example 6d and Example 71 in EP 569 337. Other preferred compounds include tetrahydropyran derivatives as disclosed in EP 626 385, e.g. the compound disclosed under Example 8 in EP 626 385.

SUMMARY OF THE INVENTION

It has now been surprisingly found that stable formulations containing [3'-desoxy-3'-oxo-MeBmt]$^1$-[Val]$^2$-Ciclosporin that have good bioavailabilty characteristics can be obtained.

DETAILED DESCRIPTION OF THE INVENTION

Figure 1:
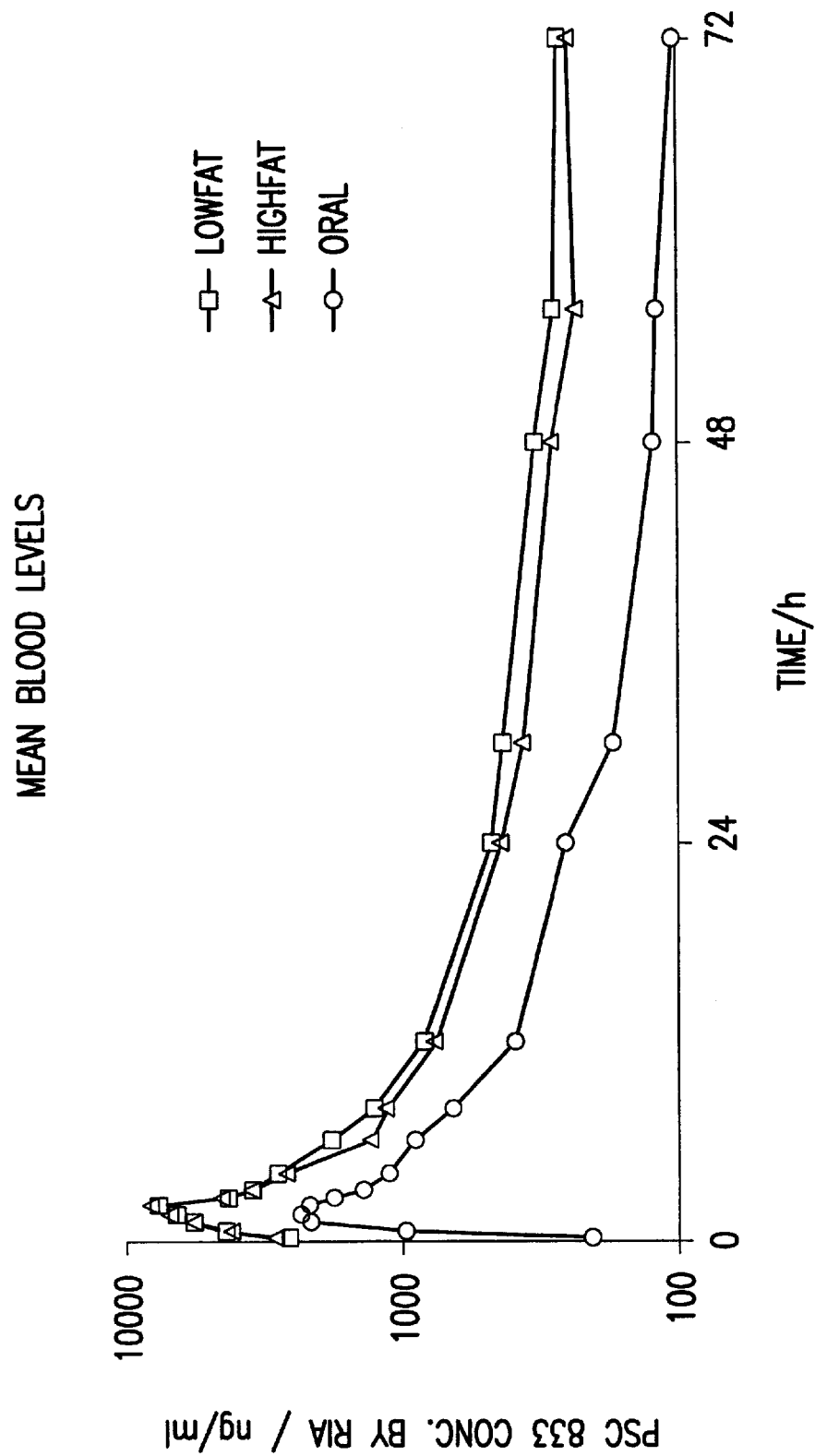
FIG. 1 is a graphical representation of the mean blood levels of cyclosporin PSC 833 in dogs as a function of time, as determined by radioimmunoassay.

Accordingly in one aspect this invention provides an intravenously or orally applicable, drug compound containing pharmaceutical fat emulsion in water, prepared by mixing a solution of a drug compound and a stabilizer with a placebo fat emulsion, the emulsion being filtrable up to 2 days through a Nuclepore$^R$ filter having a pore diameter of 0.2 micrometer without filtration residue and its fat droplets containing 0.1 to 20 percent of weight of a cyclosporin as the drug compound, related to the weight of the fat, and having a diameter of up to 500 nanometer.

In another aspect this invention provides a process for preparing an emulsion composition comprising a cyclosporin, a rapamycin or an ascomycin or a derivative thereof as active agent, which process comprises the step of admixing to a placebo fat emulsion a concentrate comprising
a) the active agent,
b) a stabiliser selected from a phospholipid, a glycolipid, a sphingolipid, a diacylphosphatidyl glycerol, an egg-phosphatidylglycerol, a soy-phosphatidylglycerol, a diacylphosphatidylglycerol, or a salt thereof; or a saturated, mono- or di-unsaturated ($C_{12-24}$) fatty acid, or a salt thereof, and
c) an organic solvent,
wherein the weight ratio of active agent to stabiliser is between 400:1 and 0.5:1.

Admixing may be carried out conveniently by injection of the concentrate into the placebo fat emulsion.

This composition provides a surprisingly high bioavailability and hence the dosage of active ingredient, e.g. [3'-desoxy-3'-oxo-MeBmt]$^1$-[Val]$^2$-Ciclosporin required to be delivered can be decreased. The composition is also convenient to use and permits efficient and consistent absorption of [3'-desoxy-3'-oxo-MeBmt]$^1$-[Val]$^2$-Ciclosporin by the body. The composition is particularly effective in treating multiple drug resistance syndrome in, for example, cancer patients undergoing chemotherapy.

The mean fat droplet size is between about 250 nm to 500 nm. Solid material having a dimension e.g. diameter >200 nm, e.g. undissolved drug compound (active agent) is collected and retained by the filter pores. The fat droplets are flexible, however, and pass through the filter pores. The mean diameter of the droplets in the fat emulsion compositions of this invention is substantially similar to the droplet diameter in the placebo emulsion. A "Nucleopore" filter is an example of a high-quality filter available commercially.

The term "placebo fat emulsion" is understood to mean a fat emulsion without active agent. Placebo fat emulsions can be prepared by known methods and are available commercially, e.g. under the trade marks Intralipid or Lipofundin.

A "pharmaceutical emulsion" is understood herein as a composition in which the individual components or ingredients are themselves pharmaceutically acceptable and, when a particular form of administration is foreseen, are suitable or acceptable for that form of administration.

The emulsion contains 1–30, preferably 8 to 20, particularly 10 to 20 and especially 10 to 16 percent by weight of fat. The fat droplets preferably have a diameter of up to 300 nanometer (=0.3 micrometer).

In addition to oral administration, intravenous administration of cyclosporins or macrolides is especially of interest, since particularly immediately after organ transplantations or in conjunction with chemotherapy oral administration may not be possible.

Since cyclosporins are insoluble in an aqueous medium, they are typically dissolved in a mixture of alcohol and poly(oxyethylene)40-castor oil in order to enable intravenous administration, and just before use diluted with brine or a glucose solution and slowly infused.

For that reason the intravenous applicable form of cyclosporin A is merely available as a concentrate (Sandimmune$_R$—infusion—concentrate) with alcohol and poly(oxyethylene)40-castor oil, which are not ideal excipients. Poly(oxythlyene)40-castor oil in injection and infusion solutions may lead to hypersensitivity reactions especially in people with allergic symptoms or in people, who shortly before have had a comparable composition with the same excipient by injection or infusion. Hypersensitivity reactions may include lowering of blood pressure, deficient blood circulation or lack of air. On longer-term use an increase of blood fat values with pathological shift of lipoprotein profile, prejudiced flowing properties of the blood and increased aggregation readiness may occur. Poly (oxyethlyene)40-castor oil, e.g. Cremophor$^R$ EL—, a nonionic emulsifier, is not a natural oil and is—in contradiction to them—soluble in water.

For the reasons above mentioned, it is of utmost importance to have available a cyclosporin containing injection or infusion solution, which does not contain poly(oxyethylene) 40-castor oil and which contains the active ingredient, e.g. cyclosporin, in amounts sufficient for a therapeutic effect and which is patient-compatible and without the side effects described above.

According to the present invention a cyclosporin- or macrolide-containing injection or infusion solution is provided in which the cyclosporin or macrolide is present in a concentration which provides therapeutical efficacy in an intravenously applicable mixture with natural excipients.

In the US Pharmacopoeia XXII, 619 a cyclosporin concentrate is described, which is a sterile solution of cyclosporin in a mixture of alcohol and a plant-oil. This composition however is not suitable for injection, since the injection of an oil in this concentrated form may cause a lethal embolism.

Since cyclosporins are soluble in natural oils, it would be obvious to dissolve them simply in fat emulsions available commercially, e.g. in Intralipid$^R$, by addition of crystalline cyclosporin. This however is not realisable, since even after intensive stirring, a predominating amount remains present in the form of undissolved crystals. A loading up of the fat droplets in the aqueous fat emulsion is hardly possible and the final result is an emulsion having an amount of cyclosporin dissolved which is insufficient for a therapeutically suitable effect and additionally contains solid cyclosporin crystal particles which may be of a dangerously large size for intravenous injection or infusion.

According to the present invention this disadvantage can be overcome, even if using PSC 833, which is more lipophilic than other cyclosporins. For this reason PSC 833 is the preferred cyclosporin compound in the emulsion of the invention.

The fat used in the placebo fat emulsion is preferably an acylglycerol or an acylglyerol having a $(C_{8-22})$-1-alkylether or -1-α,β-alkenylether group in position 1 of the glycerol part. (See Albert. L. Lehninger, Biochemie, Edition Chemie, Weinheim, New York 1979 page 230). The amount of fat used in the emulsion is preferably 1–30, particularly 8–20% by weight. Preferably the acylglycerol is without an ether group and if so, especially a di- and/or triacylglycerol having $(C_{8-22})$ fatty acid chains, particularly a di- and/or triacylglycerol mixture having a $(C_{8-12})$ fraction and a $(C_{18-22})$ fraction of fatty acid chains.

Of the fatty acid chains preferably 40–60, more preferably 45–55% by weight is unsaturated. A particularly suitable fat is soybean oil. Ready made fat emulsions, suitable as a component for the fat emulsion of the invention include commercially available products like Lipofundin 10% MCT, or Intralipid of Kabi, or Abbolipid.

Lipofundin MCT contains as an oil phase a 1:1 mixture of long chain triglycerides (LCT) and medium chain triglycerides (MCT, Miglyol 810 or 812, preponderantly consisting of caprylic/capric triglyceride). This mixture leads to a faster uptake of the fat droplets in the blood stream, thereby avoiding an impairment of the immune system of the liver function. The half-life of LCT/MCT in the blood is between 10 and 30 minutes. The fast elimination of the lipid carrier avoids its accumulation in the blood and is therefore expected to have no or minimal influence on the elimination kinetics of the drug compound during a prolonged infusion. The MCT/LCT mixture may have better solubilisation properties than LCT alone.

The placebo fat emulsion contains preferably an emulsifier, which is particularly a positively or negatively charged or a polar tenside having $(C_{12-22})$ saturated or mono- or di-unsaturated alkyl groups, especially an electrically charged phosphatide, being no zwitterion, preferably a negatively charged phosphatide.

The emulsifier is preferably present in an amount of 0.4 to 3% by weight related to the emulsion weight. A good representative of a suitable emulsifier is soya- or egg-lecithin. It contains apart from its preponderant component phosphatidylcholine with a zwitterion structure also other, negatively charged and polar components.

A polar tenside, e.g. a poloxamer, is also usable. If present, a natural surface active agent is preferred, e.g. a lecithin.

The drug-loaded fat emulsion of this invention further contains a stabiliser preferably a phospholipid or such one having a $(C_{12-22})$-1-alkylether or -1-α,β-alkenyl-ether group in position 1 (see for such special structures: Karlson, Doenecke and Koolman, Kurzes Lehrbuch der Biochemie für Mediziner und Naturwissenschaftler, 1994, page 306, FIG. 13.2, a plasmanyl—or plasmenylethanol amnine).

A glycolipid (see also Karlson, page 289, the table and page 303), a compound with a mono- or oligo-saccharide moiety instead of a phosphate variety, especially a sphingolipid (page 303, 308), e.g. sphingomyelin (page 308, 309) is also contemplated as stabiliser.

Preferably however is the use of a phospholipid, which is negatively charged, for example a diacylphosphatidyl glycerol, especially such one having an unsaturated $(C_{12-22})$ fatty acid moiety, e.g. palmitoyl oleoyl phosphatidylglycerol (hereafter POPG), egg-phosphatidylglycerol, soy-phosphatidylglycerol, or diacyl-phosphatidylglycerol, or a salt thereof, e.g. sodium-, potassium- or ammonium-POPG, more preferably NaPOPG.

Another preferred stabiliser is a saturated, mono- or di-unsaturated $(C_{12-24})$ fatty acid, especially oleic acid, or a salt thereof e.g. sodium, potassium or ammonium oleate, more preferably sodium oleate.

The stabiliser used in the present invention serves to increase the concentration of active agent in the ready-to-use fat emulsion, and to increase the rate of formation of the emulsion. Thus the active agent is incorporated stably and rapidly within the fat droplets of the placebo fat emulsion. After the ready-to-use emulsion is formed, there is no precipiatation of the active agent so that the emulsion may be administered to a patient safely. The ready-to-use emulsion may be formed rapidly, e.g. in less than or about I second or in a few seconds.

The present applicants have found, therefore, that use of the stabiliser in the compositions of this invention provides at least a two-fold, e.g. a three-fold, four-fold, five-fold or higher multiple increase of solubilisation of active agent in fat droplets of the placebo fat emulsion when compared with a simple mixture of active agent with placebo fat emulsion. Thus a concentration of at least about 5 mg PSC 833 per ml fat emulsion and up to about 20 mg/ml may be obtained. For cyclosporins, ascomycins and rapamycins, therefore, a concentration of active agent of at least about 3 mmol/liter fat emulsion, e.g. 4 mmol/liter, 5 mmol/liter or more and up to about 20 mmol/liter may be obtained.

The applicants have found that, in the absence of the stabiliser, using e.g. an ethanolic solution of active agent, a substantially lower concentration of active agent is obtained compared with that obtainable using the stabiliser. Further, there is precipitation of active agent which is unacceptable when intravenous administration is contemplated.

The drug compound containing fat emulsion additionally contains, for a larger drug compound load, an organic solvent, e.g. polyethylene glycol, e.g. polyethylene glycol 300 or 400. Ethanol and propylene glycol are also possible, e.g. in a 1:99 to 99:1 weight mixture, e.g. 25:75 to 75:25, and preferably a mixture of about 45:55 to 55:45, e.g. a 50:50 weight mixture of ethanol and propylene glycol is used, thereby recognising the good dissolving efficacy of ethanol and the undesirability of a greater alcohol concentration in the blood after administration of the emulsion.

In another aspect, this invention provides a pharmaceutical concentrate containing a cyclosporin or macrolide, e.g. a rapamycin or an ascomycin or derivative thereof, as drug compound and a stabiliser in a weight ratio of drug compound to stabiliser of from 400:1 to 0.5:1, e.g. 200:1 to 1: 1, preferably from 100:1 to 1:1, more preferably from 100: 1 to 10: 1, e.g. 50:1, 40:1, 30:1, 20:1 or 10:1, as a component for the fat emulsion of the invention.

In another aspect, this invention provides the use of a stabiliser as described herein in increasing the concentration in a ready-to-use fat emulsion of a cyclosporin, a rapamycin or an ascomycin or derivative thereof as active agent as described herein over the concentration obtainable with a placebo fat emulsion and/or accelerating formation of the ready-to-use emulsion.

In another aspect this invention provides a method for increasing the concentration in a ready-to-use fat emulsion of a cyclosporin, a rapamycin or an ascomycin or derivative thereof as active agent as described herein over the concentration obtainable with a placebo fat emulsion and/or accelerating formation of the ready-to-use emulsion by use of a stabiliser as described herein.

A product of about the same formation is generally known from UK Patent GB 2 269 536 B, but not as a starting product for incorporating into a fat emulsion. On filtration of product disclosed in GB 2 269 536 through a 200 nm pore filter, all product containing active agent, e.g. peptide, is retained on the filter.

Preferably the concentrate of this invention is present in an organic solvent in an amount of up to 20%, e.g. 0.1 to 20% by weight of the drug compound related to the concentrate weight, which solvent makes the concentrate at least intravenously applicable.

The stabiliser in the concentrate of this invention may be the phospholipid, the glycolipid or the fatty acid, if present, in the placebo fat emulsion.

The cyclosporin used in the concentrate may be cyclosporin A or PSC 833, and is preferably PSC 833. Preferred rapamycins and ascomycins are as described above.

The concentrate is prepared by mixing the drug compound and the stabiliser in an organic solvent, preferably a solvent which is also present in the drug compound containing fat emulsion described above, until complete dissolution is reached. The concentrate may be in liquid or in solid form. The solid form may be obtained by removing the organic solvent used in the production. If ethanol is used, it may be removed by evaporation, e.g. by freeze- or spray-drying.

The term "organic solvent" is understood herein to include a single component organic solvent or a mixture of two or more organic solvents.

The drug containing fat emulsion is prepared by mixing, preferably by injecting, the concentrate, whether in liquid or in solid form, preferably in liquid form (to facilitate the incorporation of the drug compound and stabilizer into the dissolved fat droplets) into the placebo fat emulsion, after which the drug containing fat emulsion, preferably up to 24 hours after its preparation may be administered to a patient.

The concentrate solution and the placebo fat emulsion may be stored in separate ampoules and are stable under normal conditions for a long period e.g. months or years.

In a preferred aspect this invention thus provides an emulsion for intravenous administration of [3'-desoxy-3-oxo-MeBmt]$^1$-[Val]$^2$-Ciclosporin as active agent comprising
a) a placebo fat emulsion, and
b) a solution in an organic solvent, e.g. comprising ethanol and/or propylene glycol, of the active agent with sodium oleate or NaPOPG as stabiliser,
wherein the weight ratio of active agent to stabiliser is from 400:1 to 10:1.

In another aspect this invention provides a process for preparing an emulsion for intravenous administration of [3'-desoxy-3-oxo-MeBmt]$^1$-[Val]$^2$-Ciclosporin as active agent which process comprises the step of admixing to a placebo fat emulsion a concentrate comprising
a) the active agent and
b) sodium oleate or NaPOPG as stabiliser,
c) an organic solvent, e.g. comprising ethanol and/or propylene glycol,
wherein the weight ratio of active agent to stabiliser is from 400:1 to 10:1.

The invention thus also provides a set of ampoules containing the concentrate and bottles containing a placebo fat emulsion, suitable for mixing their contents in proportions which meet the needs of a patient concerning the required amount of drug compound in a pharmaceutically safe particle size.

In addition to intravenous administration, the applicants contemplate oral administration of a concentrate or emulsion of this invention, e.g. in a flavoured drink solution or milk; nasal administration; via inhalation; or topically, e.g. dermally.

The pharmaceutical cyclosporin or macrolide-containing fat emulsions are used for the same indications as known formulations for the respective cyclosporin or macrolide and in the same manner.

The exact dosage to be used may be determined in conventional manner, e.g. in standard bioavailability tests in animals, e.g. dogs. In general the dosages are from about 100% to 200% that of known formulations.

The compositions of this invention are useful for the known indications of the cyclosporin, or macrolide e.g. rapamycin, e.g. for the following conditions:
a) Treatment and prevention of transplant rejection, e.g. organ or tissue allo- or xeno-transplant rejection, e.g. for the treatment of recipients of e.g. heart, lung, combined heart-lung, liver, kidney, pancreatic, skin or corneal transplants. They are also indicated for the prevention of graft-versus-host disease, such as following bone marrow transplantation.
b) Treatment and prevention of autoimmune disease and of inflammatory conditions, in particular inflammatory conditions with an etiology including an autoimmune component such as arthritis (for example rheumatoid arthritis, arthritis chronica progrediente and arthritis deformans) and rheumatic diseases. Specific autoimmune diseases for which the compounds of the invention may be employed include, autoimmune hematological disorders (including e.g. hemolytic anaemia, aplastic anaemia, pure red cell anaemia and idiopathic thrombocytopenia), systemic lupus erythematosus, polychondritis, sclerodoma, Wegener granulamatosis, dermatomyositis, chronic active hepatitis, myasthenia gravis, psoriasis, Steven-Johnson syndrome, idiopathic sprue, autoimmune inflammatory bowel disease (including e.g. ulcerative colitis and Crohn's disease) endocrine ophthalmopathy, Graves disease, sarcoidosis, multiple sclerosis, primary billiary cirrhosis, juvenile diabetes (diabetes mellitus type I), uveitis (anterior and posterior), keratoconjunctivitis sicca and vernal keratoconjunctivitis, interstitial lung fibrosis, psoriatic arthritis, glomerulonephritis (with and without nephrotic syndrome, e.g. including idiopathic nephrotic syndrome or minimal change nephropathy) and juvenile dermatomyositis.
c) Treatment and prevention of asthma.
d) Treatment of multi-drug resistance (MDR). The compositions are therefore useful for enhancing the efficacy of other chemotherapeutic agents in the treatment and control of multidrug resistant conditions such as multidrug resistant cancer or multidrug resistant AIDS.
e) Treatment of proliferative disorders, e.g. tumors, hyperproliferative skin disorder and the like.
f) Treatment of fungal infections.
g) Treatment and prevention of inflammation, especially in potentiating the action of steroids.

h) Treatment and prevention of infection, especially infection by pathogens having Mip or Mip-like factors.

i) Treatment of overdoses of FK-506 and other macrophilin binding immunosuppressants.

The compositions of the ascomycin, FK506 or ascomycin derivatives disclosed herein are useful, for example, in the treatment of inflammatory and hyperproliferative skin diseases and of cutaneous manifestations of immunologically-mediated diseases. More specifically, the compositions of this invention are useful as antiinflammatory and as immunosuppressant and antiproliferative agents for use in the prevention and treatment of inflammatory conditions and of conditions requiring immunosuppression, such as a) the prevention and treatment of rejection of organ or tissue transplantation, e.g. of heart, kidney, liver, bone marrow and skin, graft-versus-host disease, such as following bone marrow grafts, autoimmune diseases such as rheumatoid arthritis, systemic lupus erythematosus, Hashimoto's thyroidis, multiple sclerosis, Myasthenia gravis, diabetes type I and uveitis, cutaneous manifestations of immunologically-mediated illnesses;

b) the treatment of inflammatory and hyperproliferative skin diseases, such as psoriasis, atopical dermatitis, contact dermatitis and further eczematous dermatitises, seborrhoeic dermatitis, Lichen planus, Pemphigus, bullous Pemphigoid, Epidermolysis bullosa, urticaria, angioedemas, vasculitides, erythemas, cutaneous eosinophilias, Lupus erythematosus and acne; and c) Alopecia areata.

The exact amount of the compositions to be administered depends on several factors, for example the desired duration of treatment and the rate of release of the active ingredient.

The utility of the pharmaceutical compositions can be observed in standard clinical tests in, for example, known indications of active agent dosages giving equivalent blood levels of active agent; for example using dosages in the range of 1 mg to 1000 mg, e.g. 5 mg to 100 mg, of active agent per day for a 75 kilogram adult and in standard animal models. The increased bioavailability of the drug substance provided by the compositions can be observed in standard animal tests and in clinical trials. For example an indicated adult daily dose following renal transplantation is from 50 to 200 mg/day.

Advantages of the process and compositions of this invention include:

few excipients in the active agent concentrate;

rapid formation of the ready-to-use emulsion;

no precipitation of active agent in the ready-to-use emulsion;

narrow droplet size distribution in the ready-to-use emulsion;

high concentration of active agent in emulsion; and the fat emulsion is ready for use after gentle shaking after mixing placebo emulsion with active agent concentrate.

Following is a description by way of example only of compositions of the invention.

EXAMPLES

1. PSC 833 Containing Concentrate to be Introduced into a Placebo Fat Emulsion

|                  | mg/ml |                  |
| ---------------- | ----- | ---------------- |
| PSC 833          | 100   | 10.87% by weight |
| Sodium oleate    | 10    | 1.09% by weight  |
| Ethanol          | 410   | 44.56% by weight |
| Propylene glycol | 400   | 43.48% by weight |
|                  | 920   | 100.00           |

2. Fat Emulsion Containing PSC 833

The concentrate of Example 1 may be introduced into Lipofundin$^R$ MCT 10%, a placebo fat emulsion, e.g. by injection at a dilution factor of about 17, giving the following composition:

|                          | mg/ml |
| ------------------------ | ----- |
| PSC 833                  | 5.9   |
| Sodium oleate            | 0.59  |
| Ethanol                  | 24.4  |
| Propylene glycol         | 23.8  |
| Lipofundin MCT 10%       |       |
| components:              |       |
| MCT/LCT                  | 94.3  |
| Egg phosphatidyl choline | 11.3  |
| Glycerol                 | 23.6  |
| Sodium oleate            | 0.28  |

107 ml of the PSC 833 containing fat emulsion (obtained from 7 ml of the concentrate and 100 ml of Lipofundin$^R$ MCT 10%) is a sufficient dosage for a patient of 70 kg of body weight, leading to a moderate load of 10 g of fat, 2,6 g of ethanol, 2.5 g of propylene glycol and 631 mg of PSC 833 per day, since the necessary dosage by injection is 9 mg PSC 833 per kg of body weight, which is for a patient of 70 kg of body weight 630 mg. For oral use 20 mg PSC 833 per kg of body weight per day is necessary. A patient of 70 kg of body weight thus needs about 1400 mg PSC 833 for oral use, in a fat emulsion, which may be prepared by mixing of 14 ml of the concentrate of Example 1 with 100 ml or more of Lipofundin$^R$ 10% MCT.

For medical use, the required amount of drug solution may be taken from a 5 ml ampoule containing 500 mg of PSC 833 concentrate and/or of a 2.5 mg ampoule containing 250 mg PSC A-833 and may be introduced by injection into 100 ml of Lipofundin$^R$ MCT 10% whereafter the combined mixture may be administered to a patient by infusion or oral application.

Since conventional fat emulsions with cyclosporins lack the required physical stability needed for a drug product (crystal formation at the required level drug loading), the loading of a conventional placebo fat emulsion (intended for parenteral nutrition) with PSC 833 was investigated without and in the presence of stabilizers within the 24 hours, that it must be administered to a patient. The solubilization efficacy was determined by filtering the drug loaded fat emulsion through a 0.2 micron Nuclepore filter. Drug compound which is not solubilized was held back by the filter and determined gravimetrically and/or by HPLC measurements.

Injection of a plain PSC 833 solution in ethanol into a fat emulsion leads to incomplete solubilization: only 87% is solubilized after 30 minutes (see table). The reason for this incomplete solubilization is fast precipitation of the drug compound before all PSC 833 molecules have reached the oil droplets. In another experiment and according to the invention it was tried to stabilize these PSC 833 precipitates in the fat emulsion with the sodium salt of palmitoyl-oleoyl phosphatidyl glycerol (POPG.Na). Further sodium oleate was used, instead of POPG.Na.

Addition of POPG.Na (Nippon Fine Chemical) or sodium oleate (Fluka, purity >99%) led surprisingly to a complete solubilization of PSC 833. After 5 minutes less than 0.1% is retained on the filter, as determined by HPLC. Sodium oleate and POPG.Na appeared to be equally well suited for obtaining the complete solubilization of PSC 833. Propylene glycol was then used to replace a part of the ethanol content.

In using Lipofundin$^R$ 10% MCT it was found that the fat phase can be loaded with PSC 833 up to 20%. This means that up to 2 gram of PSC 833 can be solubilized by 100 ml of a 10% fat emulsion.

Determination of the solubilization of PSC 833 in fat emulsions*: influence of excipients in the concentrate. Compositions 3 to 7 and 8 to 12 are those according to the invention

| | Mixtures with weight ratio of compounds | Non solubilized PSC 833 recovered on the 0.2 micron filter (time-point of filtration) as wt-% of initial amount |
|---|---|---|
| 1 | 1 PSC833/EtOH-90[#] 10/90 + 20 Intralipid 10% | 13% (30 min) |
| 2 | 1 PSC 833/oleic acid/EtOH-90[#] 10/1/89 + 20 Intralipid 10% | 20% (5 min), 12.3% (30 min) |
| 3 | 1 PSC 833/POPG.Na/EtOH-90[#] 10/1/89 + 20 Intralipid 10% | 0.6% (3 min), 0.2% (6 min) 0.06% (15 min, 24 hours, 12 days at RT) |
| 4 | 1 PSC 833/Na.OL/EtOH-90[#] 10/1/89 + 20 Intralipid 10% | 0.05% (5 min) |
| 5 | 1 PSC 833/NaOL/PG/EtAbs 10/1/40/41 + (slow injection) 20 Lipofundin ® MCT 10% | 0.06%, 0.2% (3 min) |
| 6 | 1 PSC 833/NaOL/PG/EtAbs[#] 10/1/40/41 + 10 Lipofundin ® MCT 10% | 0.1%, 0.1% (3 min) |
| 7 | 1 PSC 833/NaOL/PG/EtAbs[#] 10/1/40/41 + 5 Lipofundin ® MCT 10% | 0.13%, 0.1% (3 min) |

Compositions 8 to 12

| active agent to stabiliser ratio | | Non-solubilized PSC 833 recovered on the 0.2 micron after (figure in brackets is time-point after commencement of filtration) |
|---|---|---|
| Example 8 | | |
| 10:1 | 1 PSC 833/POPG.Na/PG/EtAbs[#] 10/1/40/41 + 10 Lipofundin ® MCT 10% | <1% (5 min), <1% (1 hour) (relative component amounts in concentrate by weight) |
| Example 9 | | |
| 50:1 | 1 PSC 833/POPG.Na/PG/EtAbs[#] 10/0.2/40/41 + 10 Lipofundin ® MCT 10% | <1% (5 min), <1.6 % (16 hour) (relative component amounts by wt) |
| Example 10 | | |
| 400:1 | 1 PSC 833/POPG.Na/pG/EtAbs[#] 10/0.025/40/41 + 10 Lipofundin ® MCT 10% | <1% (5 min), <1% (1 hour) (relative amounts by weight) |
| Example 11 | | |
| 1:1 | 1 PSC 833/POPG.Na/PG/EtAbs[#] 10/10/40/41 + 10 Lipofundin ® MCT 10% | <1% (5 min), <1% (1 hour) (relative amounts by weight) |
| Example 12 | | |
| 0.5:1 | 1 PSC 833/POPG.Na/PG/EtAbs[#] 10/20/40/41 | <1% (5 min), <1% (1 H) (relative amounts by weight) |

-continued

Determination of the solubilization of PSC 833 in fat emulsions*: influence of excipients in the concentrate. Compositions 3 to 7 and 8 to 12 are those according to the invention

| Mixtures with weight ratio of compounds | Non solubilized PSC 833 recovered on the 0.2 micron filter (time-point of filtration) as wt-% of initial amount |
|---|---|
| + 10 Lipofundin ® MCT 10% | |

*drug loaded fat emulsions are filtered through a 0.2 micron Nucleopore filter
NaOL = sodium oleate; PG = propylene glycol; EtOHAbs = ethanol absolute; EtOH90 = ethanol with 10% water; RT = Room temperature The mean particle size (250 mm) and the particle size distribution (unimodal distribution, all particles smaller than 500 mm) were determined by photon correlation spectroscopy.

When e.g. 5 or 10 ml of the concentrate of this invention are injected fast into 100 ml of Lipofundin$^R$ MCT 10% and mixed subsequently, the mixture is physical-chemical stable at room temperature for 48 hours (mixtures 5 and 6).

Example 13

Dog Study

A pharmacokinetic study was performed with beagle dogs, using as reference an oral form in order to determine whether the fat emulsions carriers used, applied intravenously, have an influence on elimination kinetics. Following compositions were prepared:

13a ("low-fat" form)

100 mg PSC 833 in a fat emulsion: 1 mL of the concentrate composition described as no. 5 and 6 above was diluted with 10 parts of Lipofundin MCT 10%.

13b ("high-fat" form)

100 mg PSC 833 in a fat emulsion: 1 mL of of the concentrate composition described as no. 5 and 6 above was diluted with 20 parts of Lipofundin MCT 10%.

13c 200 mg PSC 833 are administered in an oral drink having the following composition:

| propylene glycol | 96 mg |
|---|---|
| Labrafil M2125 CS (interesterified corn oil) | 150 mg |
| Cremophor RH40 (polyoxyl-40 hydrogenated castor oil) | 524 mg |
| PSC 833 | 100 mg |
| DL-alpha-tocopherol | 1 mg |
| ethanol abs. | 104 mg | by administration using 2 hard gelatin capsules.

A cross over study was performed with 4 dogs and the formulations were administered to fasted dogs either by slow infusion (compositions 13a and 13b: duration 2 hours) or orally (13c). No significant formulation-dependent side effects were observed. Blood concentration is determined by radioimmunoassay (RIA) and results of the three administered compositions are shown graphically in FIG. 1.

Concentration in blood of active agent (PSC 833 abbreviated "PSC") is plotted on a log scale on the vertical axis. Time in hours after commencement of administration is plotted on the horizontal axis. As is apparent from the gradient of each graph in FIG. 1, no significant differences in elimination kinetics between the 3 forms are observed. The gradient of each graph appears similar one with another from about 2 hours, i.e. end of infusion. Surprisingly there appears to be no significant influence of the fat-emulsion on the elimination kinetics the lipophilic compound PSC. Elimination kinetics of the injectable forms appear similar to those of the oral form.

Example 14

Fat emulsions are prepared using as active agent the compound (compound A) disclosed in Examples 6d and 71 of published European patent application EP 569337.

Concentrate containing compound A as active agent

| | mg/ml | |
|---|---|---|
| compound A | 100 | 10.87% by weight |
| sodium oleate | 10 | 1.09% by weight |
| ethanol | 410 | 44.56% by weight |
| propylene glycol | 400 | 43.48% by weight |
| | 920 | 100.00 |

Determination of the solubilisation of compound A in fat emulsions*: influence of excipients in the concentrate. Composition 14a is according to the invention

| Mixtures | Non-solubilized compound A recovered on 0.2 micron filter (time-point of filtration) |
|---|---|
| 14a with stabiliser | |
| 1 compound A/NaOL/PG/ EtAbs# 10/1/40/41 + 20 Lipofundin MCT 20% | <1.0% (5 min), <2.5% (18 hours) |
| 14b without stabiliser | |
| 1 compound A/PG/EtAbs# 10/40/41 + 20 Lipofundin ® MCT 20% | 7.4% (5 min), 12% (1 hour) |

*active agent-loaded fat emulsions are filtered through a 0.2 micron filter (a Nucleopore filter)
NaOL = sodium oleate; PG = propylene glycol; EtOHAbs = ethanol absolute.

Examples 15 to 54

Analogous compositions are prepared to compositions 3 to 12 above for other active agents by replacing the active agent PSC by 40-O-(2-hydroxy)ethyl rapamycin (Examples 15 to 24), 32-deoxorapamycin (Examples 25 to 34), 16-pent-2-ynyloxy-32(S)-dihydrorapamycin (Examples 35 to 44), and 33-epi-chloro-33-desoxy-ascomycin (Examples 45 to 54). Stable emulsion compositions are obtained rapidly on admixing, by injection, the respective active agent concentrate into placebo fat emulsion.

Compositions, which, to a certain extent, are comparable with the drug compound containing fat emulsions of the invention and with the concentrates are described in the literature:

According to EP 0570829 A1 an intravenously applicable fat emulsion is described which contains a cyclosporin, a natural oil, a phosphatidyl choline, a phosphatidylethanolamine and water, plus—optionally—an alkali salt of a fatty acid. According to Example 5 an emulsion containing 4 percent of weight of a cyclosporin related to the oil weight is prepared by dissolution of the cyclosporin in the oil phase and subsequent emulsification in the water phase which contains all other excipients mentioned above. A disadvantage of the fat emulsion is that if higher cyclosporin concentrations are strived for, only a part of the cyclosporin amount is dissolved. The other part is present in solid form in the inner part of the fat particle (see page 4, lines 41–46).

The composition of Example 5 is filtered through a filter, having a pore diameter of 5 microns (see page 5. line 38). The particle size of solid particles which may be present (see page 8, table) is therefore allowed to be larger than the particle size of the composition of the instant invention, which particles without filtration residue are filtered through a filter having a pore diameter of 0.2 micrometer. The intravenously applicability of the emulsions of EP 0570829 A1 is thus not without any danger. A further disadvantage is particularly that when higher drug loading of the oil phase is strived for, the drug compound tends to precipitate during storage for more than 3 months.

According to EP 0331755 B1 a drug compound containing fat emulsion is described which in contrast to the compositions of the present invention, contains no POPG.Na, sodium oleate or other stabilizers, which makes it impossible to prepare cyclosporins incorporated at a satisfactory percentage in the fat droplets, without having a certain percentage present in the water phase due to precipitation before incorporation into the fat droplets.

The fat emulsion thus may, just as the emulsion described before, contain particles which can not be administered without any potential danger, especially if the emulsion has a larger drug loading concentration.

Derwent Abstract 92-352740 (JP 042253907-A) is related to a fat emulsion containing a cyclosporin as the drug compound, a phosphatidyl choline (lecithin), sodium oleate, soybean oil, glycerol and water and is meant for intravenous application. The fat emulsion contains 0.2% of weight of the cyclosporin related to the emulsion weight and 2% of cyclosporin related to the fat, e.g. soybean oil.

According to the present invention a fat emulsion is available, which has, with a comparable amount of drug compound, an excipient load related to the fat amount, of one tenth of that in hitherto known compositions.

The fat emulsion of the art is produced starting from all the different components, which are mixed in a homogenizer under high pressure. Since it is produced in one step, it is comparable with the emulsion of EP 0570829 A1, described before and has the same disadvantage of tending to exhibit precipitation of active ingredient.

The composition of the present invention has the advantage of being safe, is prepared shortly before administration, e.g. a few minutes or about one hour, and is formulated by mixing two separate units, i.e. concentrate and placebo fat emulsion which each are stable for long periods, particularly in ampoules, and which can be simply mixed by injection of the concentrate into the fat emulsion without using an homogenizer.

According to EP 0317120 A1 Amphotericin is transformed into a water soluble complex, with a phosphatidyl glycerol in an acid medium, optionally in the presence of phosphatidyl choline and of cholesterol. In the representative Example 1 the molar ratio is 0.4 parts of Amphotericin: 0.8 parts of distearoyl phosphatidyl glycerol: 2.0 parts of hydrogenated egg phosphatidyl choline: 1.0 parts of cholesterol (see page 7, table and also claim 7). The pH is 4.5. The amounts of excipients are so large that upon addition of an aqueous phase to this pharmaceutical intermediate, liposomes (see page 2, line 5) are formed which incorporate the drug compound. According to the present invention the pH is preferably not in the acid range. From this pharmaceutical mixture which is merely an intermediate, in subsequent manufacturing steps, which are different from those of the invention, liposomes are produced which may be stabilized by lyophilization to guaranteee an adequate shelf life.

According to example 3 of PCT application WO 88/06438, colloidal particles of the drug compound cyclosporin A, which is very poorly soluble in water, together with a stabilizer are prepared in a weight ratio of active substance: stabilizer of 2:1 and with diameters of about 1.0 micrometers and thus lie inside the drug compound: stabilizer weight ratio of the concentrate used as a component for the fat emulsion according to the invention. A solution of the cyclosporin and the stabilizer in absolute ethanol and polyethylene glycol 400 is injected in dextrose containing water leading to a suspension of stabilized colloidal particles and not, as according to the present invention, into a fat emulsion. However, the stabilizer consisting of phosphatidyl-choline does not have electrostatically stabilizing activity, since it is a zwitterion. The stabilizer contains a portion of insoluble phospholipids which become charged in the

What is claimed is:

1. A concentrate comprising
    a) [3'-desoxy-3-oxo-MeBmc]$^1$-[Val]$^2$-Ciclosporin as active agent,
    b) a stabiliser selected from oleic acid or a salt thereof, or palmitoyl oleoyl phosphatidylglycerol (POPG) or a salt thereof as a stabiliser, and
    c) ethanol which concentrate is free of poly(oxyethylene)-40-castor oil and wherein the weight ratio of active agent to stabiliser is from 400:1 to 10:1.

2. A concentrate a claimed in claim 1 which further comprises propylene glycol.

3. A concentrate as claimed in claim 1 wherein the stabiliser comprises sodium oleate.

4. A concentrate as claimed in claim 1 wherein the stabiliser comprises sodium POPG.

5. An emulsion for intravenous administration comprising the concentrate of claim 1 and a placebo fat emulsion.

6. A method of treatment and prevention of transplant rejection, autoimmune disease and of inflammatory conditions which method comprises administering an effective amount a concentrate of claim 1 to a subject in need of such treatment.

7. A concentrate consisting essentially of
    a) a[3'-desoxy-3-oxo-MeBmt]$^1$-[Val]$^2$-Cicolosporin as active agent,
    b) oleic acid or salt thereof, or palmitoyl oleoyl phosphatidylglycerol (POPG) or a salt thereof as a stabiliser, and
    c) ethanol wherein the weight ratio of active agent to stabiliser is from 400:1 to 10:1.

* * * * *